United States Patent
Hulse et al.

(10) Patent No.: US 8,217,208 B2
(45) Date of Patent: Jul. 10, 2012

(54) ISOMERIZATION OF 1-CHLORO-3,3,3-TRIFLUOROPROPENE

(75) Inventors: Ryan Hulse, Getzville, NY (US); Rajiv R. Singh, Getzville, NY (US); Konstantin A. Pokrovski, Orchard Park, NY (US); Hsueh Sung Tung, Getzville, NY (US); Daniel Merkel, Orchard Park, NY (US); Haiyou Wang, Amherst, NY (US); Michael Van Der Puy, Amherst, NY (US)

(73) Assignee: Honeywell International, Inc., Morristown, NJ (US)

( * ) Notice: Subject to any disclaimer, the term of this patent is extended or adjusted under 35 U.S.C. 154(b) by 421 days.

(21) Appl. No.: 12/633,420

(22) Filed: Dec. 8, 2009

(65) Prior Publication Data

US 2010/0152504 A1 Jun. 17, 2010

Related U.S. Application Data

(60) Provisional application No. 61/122,218, filed on Dec. 12, 2008.

(51) Int. Cl.
*C07C 17/00* (2006.01)
(52) U.S. Cl. ........................................ 570/236
(58) Field of Classification Search .................. 570/236
See application file for complete search history.

(56) References Cited

U.S. PATENT DOCUMENTS

| | | | |
|---|---|---|---|
| 2,834,748 A | 5/1958 | Bailey et al. |
| 2,846,458 A | 8/1958 | Haluska, Loren A. |
| 2,889,379 A | 6/1959 | Ruh et al. |
| 2,917,480 A | 12/1959 | Bailey et al. |
| 4,465,786 A | 8/1984 | Zimmer et al. |
| 4,798,818 A | 1/1989 | Baizer et al. |
| 5,096,933 A | 3/1992 | Volkert |
| 5,137,932 A | 8/1992 | Behme et al. |
| 5,182,309 A | 1/1993 | Hutzen |
| 5,574,192 A | 11/1996 | VanDerPuy et al. |
| 5,710,352 A | 1/1998 | Tung |
| 5,900,185 A | 5/1999 | Tapscott |
| 6,111,150 A | 8/2000 | Sakyu et al. |
| 6,362,383 B1 | 3/2002 | Wilmet et al. |
| 6,844,475 B1 | 1/2005 | Tung et al. |
| 7,126,036 B2 | 10/2006 | Wegner et al. |
| 7,179,949 B2 | 2/2007 | Wilmet et al. |
| 2007/0007488 A1 | 1/2007 | Singh et al. |
| 2007/0010592 A1 | 1/2007 | Bowman et al. |
| 2007/0112228 A1 | 5/2007 | Mukhopadhyay et al. |
| 2007/0197842 A1 | 8/2007 | Mukhopadhyay et al. |
| 2008/0007788 A1 | 1/2008 | Good et al. |
| 2008/0051610 A1 | 2/2008 | Wang et al. |
| 2008/0051611 A1 | 2/2008 | Wang et al. |
| 2008/0098755 A1 | 5/2008 | Singh et al. |
| 2008/0099190 A1 | 5/2008 | Singh et al. |
| 2008/0103342 A1 | 5/2008 | Wang et al. |
| 2008/0194888 A1 | 8/2008 | Merkel et al. |
| 2008/0207788 A1 | 8/2008 | Bowman et al. |
| 2009/0270661 A1 | 10/2009 | Wang et al. |

FOREIGN PATENT DOCUMENTS

| EP | 0 974 571 | 1/2000 |
|---|---|---|
| WO | WO 2007/002703 | 1/2007 |

*Primary Examiner* — Jafar Parsa
(74) *Attorney, Agent, or Firm* — Faegre Baker Daniels LLP

(57) ABSTRACT

Disclosed are processes for an isomerization reaction between (E)1-chloro-3,3,3-trifluoropropene and (Z)1-chloro-3,3,3-trifluoropropene. Some of the disclosed processes include the step of contacting a feed stream with a heated surface, where the feed stream includes (E)1-chloro-3,3,3-trifluoropropene, (Z)1-chloro-3,3,3-trifluoropropene or mixtures thereof. The resulting product stream includes (E)1-chloro-3,3,3-trifluoropropene and (Z)1-chloro-3,3,3-trifluoropropene, where the ratio of (E) isomer to (Z) isomer in the product stream is different than the ratio feed stream. The (E) and (Z) isomers in the product stream may be separated from one another.

25 Claims, No Drawings

ISOMERIZATION OF 1-CHLORO-3,3,3-TRIFLUOROPROPENE

CROSS-REFERENCE TO RELATED APPLICATION

The present application claims the benefit of U.S. Provisional Application No. 61/122,218, titled Isomerization of 1-chloro-3,3,3-trifluoropropene, filed on Dec. 12, 2008, which is incorporated herein by reference in its entirety.

BACKGROUND OF THE INVENTION

Chlorofluorocarbon (CFC) based chemicals have found widespread use in industry in a variety of different applications including as refrigerants, aerosol propellants, blowing agents and solvents, among other uses. However, the use of certain ozone-depleting CFCs have been curtailed in favor of more commercially acceptable chemicals. One example is 1-chloro-3,3,3-trifluoropropene (hereinafter "1233zd"), which has two isomers (1233zd(Z) and 1233zd(E)). Because of the different physical properties between the two isomers, pure 1233zd(E), pure 1233zd(Z), or certain mixtures of the two isomers may be suitable for particular applications as refrigerants, propellants, blowing agents, solvents, or for other uses. There is a need for processes that selectively provide one or both of the commercially desirable isomers of 1233zd.

SUMMARY OF THE INVENTION

The present invention provides a process for conversion between 1233zd(Z) and 1233zd(E). In some embodiments, the process includes providing a feed stream consisting essentially of 1233zd(E) or a mixture of 1233zd(E) and 1233zd(Z) having less than about 5 wt % 1233zd(Z). The process also includes the step of contacting the feed stream with a heated surface that is maintained between 150° C. and 350° C. The feed stream is contacted with the heated surface for a period of time sufficient to convert at least a portion of the 1233zd(E) to 1233zd(Z) to produce a product stream. The product stream is then processed in a separation operation to separate the (E) and (Z) isomers from one another.

In other embodiments, the feed stream consists essentially of 1233zd(Z) or a mixture of 1233zd(E) and 1233zd(Z) having more than about 15 wt % 1233zd(Z). The process also includes the step of contacting the feed stream with a heated surface that is maintained between 50° C. and 350° C. The feed stream is contacted with the heated surface for a period of time sufficient to convert at least a portion of the 1233zd(Z) to 1233zd(E) to produce a product stream. The product stream is then processed in a separation operation to separate the (E) and (Z) isomers from one another.

In some embodiments, the heated surface includes an outer surface of a packing material. In some embodiments, the packing material comprises stainless steel, while in other embodiments the packing material includes a catalyst such as one or more of metal oxides, halogenated metal oxides, Lewis acid metal halides, zero-valent metals, or any combination of these catalysts.

DETAILED DESCRIPTION

Because many CFCs are known to be ozone-depleting compounds, the use of these compounds has been curtailed in favor of chemicals that are more commercially acceptable. In some cases, alternate CFC compounds have been found to be both effective and more environmentally friendly. As one example, 1-chloro-3,3,3-trifluoropropene (hereinafter "1233zd") has been found to have a wide variety of uses, for example as a heat transfer agent, as a foaming agent, and as a solvent, among other uses. U.S. Patent Publication Nos. 2008/0098755, entitled "Heat Transfer Methods Using Heat Transfer Compositions Containing Trifluoromonochloropropene," and 2008/0207788, entitled "Foaming Agents, Foamable Compositions, Foams and Articles Containing Fluorine Substituted Halogens, and Methods of Making the Same" and U.S. Pat. No. 6,362,383, entitled "Hydro-Fluorination of Chlorinated Hydrocarbons" disclose examples of such uses. 1233zd may be produced by a number of different methods. For example, Patent Application No. 61/047,613, entitled "Process for Dehydrofluorination of 3-chloro-1,1,13-tetrafluoropropane to 1-chloro-3,3,3-trifluoropropene"; U.S. Pat. No. 5,710,352, entitled "Vapor Phase Process for Making 1,1,1,3,3-pentafluoropropane and 1-chloro-3,3,3-trifluoropropene," U.S. Pat. No. 6,111,150, entitled "Method for Producing 1,1,1,3,3-pentafluoropropane," and U.S. Pat. No. 6,844,475, entitled "Low Temperature Production of 1-chloro-3,3,3-trifluoropropene (HCFC-1233ZD)" describe several methods for making 1233zd. All of these patent documents are herein incorporated by reference in their entirety.

1233zd has two isomers with different physical properties. As one example of the different properties between the two isomers, 1233zd(Z) has a boiling point of approximately 38° C., whereas 1233zd(E) has a boiling point of approximately 19° C. In some applications, it is desirable to use either pure 1233zd(E), pure 1233zd(Z), a particular blend of the (Z) and (E) isomers, or a particular blend of one or both of the 1233zd isomers and another compound in order to control the properties of the solution. For example, in some solvent applications, it is desirable to have a relatively high boiling point. In some such applications, pure 1233zd(Z) may have more desirable physical properties (e.g., a higher boiling point) than either pure 1233zd(E) or mixtures of the two 1233zd isomers.

In some prior art isomerization reactions, reagents (defined herein as any chemically reactive materials, i.e., not the 1233zd itself or the various catalysts described herein) are used to facilitate the isomerization of the 1233zd. For example, in one prior art isomerization reaction bromine is added to 1233zd(E) in order to isomerize 1233zd. In some embodiments of the present invention, the isomerization reaction is reagent-free, or it does not require the use of any reagents. As further described below, in some embodiments the absence of reagents facilitates the production of pure 1233zd, and more particularly may facilitate the production of pure 1233zd(Z) and pure 1233zd(E).

As further described below, in some embodiments of the present invention the feed stream consists essentially of either 1233zd(Z), 1233zd(E), or a mixture thereof. However, in some embodiments the feed streams may contain materials other than 1233zd(Z) or 1233zd(E). For example, the feed stream may contain less than 5 wt % (at least 95 wt % 1233zd), less than 3 wt % (at least 97 wt % 1233zd), less than 2 wt % (at least 98 wt % 1233zd), less than 1.5 wt % (at least 98.5 wt % 1233zd), or less than 1 wt % (at least 99 wt % 1233zd) of other compounds such as hydrofluorocarbons, hydrochlorocarbons, hydrochlorofluorocarbons, halogenated olefins, or other compounds. Some of these compounds may be byproducts or unreacted compounds from the production of the 1233zd. In some embodiments, these compounds do not significantly affect the isomerization reactions described herein. In other embodiments, some of these compounds may react with the 1233zd or with other compounds within an isomerization reaction, and in the process may affect the yield or purity of a product stream from the isomerization reaction.

According to some embodiments of the invention, a method is provided for converting between the (Z) and (E) isomers of 1233zd. The method includes an isomerization reaction that has a thermodynamic equilibrium at which an equilibrium ratio of (E) isomer to (Z) isomer is present. As indicated by the examples described below, the equilibrium ratio may vary depending on certain reaction conditions, including the temperature, the type and configuration of the reactor vessel, and/or the presence of one or more catalysts. If the ratio of Z to E isomer is greater than the equilibrium ratio, then at least a portion of the 1233zd(Z) is converted into 1233zd(E). In other embodiments in which the ratio of Z to E isomer is less than the equilibrium ratio, at least a portion of the 1233zd(E) is converted into 1233zd(Z).

In some embodiments, the method includes controlling the temperature of a heated surface to greater than 50° C. The heated surface is contacted with a feed stream consisting essentially of 1233zd(E) or a mixture of (E) and 1233zd(Z). The feed stream is contacted with the heated surface for a period of time sufficient to convert at least a portion of the 1233zd(E) to 1233zd(Z) to produce a product stream. In other embodiments, the heated surface is contacted with a feed stream consisting essentially of 1233zd(Z) or a mixture of (E) and 1233zd(Z). The feed stream is contacted with a heated surface for a period of time sufficient to convert at least a portion of the 1233zd(Z) to 1233zd(E) to produce a product stream.

In some embodiments, the heated surface includes the inside of a reactor vessel. In addition, or in the alternative, the heated surface may include an outer surface of a packing material, for example a packing material that is packed in a reaction vessel. In some embodiments, the reactor vessel is a batch-wise reactor vessel that can be charged with the feed stream. In some such embodiments, the feed stream may be sealed in the batch-wise reactor, and, after sufficient time passes to isomerizes the desired amount of 1233zd, the reactor vessel may be opened to remove the product stream. In other embodiments, the reactor vessel is a continuous-type reactor vessel, for example a reactor vessel with a first opening and a second opening and a fluid pathway between the first and second openings. The feed stream is fed into the reactor vessel through the first opening and passes through the reactor vessel at a rate sufficient to isomerize the desired amount of 1233zd. The resulting product stream exits the second opening. In one example, the reactor vessel is an elongate reactor vessel (e.g., a MONEL™ tube) with the first opening at a first end and the second opening at a second end.

In some embodiments, the reactor vessel may be partially or entirely packed with packing material, for example with a stainless steel packing. In some embodiments, the relatively large surface area of the packing material may facilitate the conversion reaction between the (E) and (Z) isomers. Support structures that support the packing material may also be disposed in or on the reactor vessel. For example, the packing material may be supported by a mesh or other structure that is disposed under, around, and/or within the packing material. The support structure may comprise the same material as the packing material (e.g., stainless steel), nickel, or any other suitable material.

The packing materials may also comprise one or more catalyst materials. Examples of suitable catalysts for the isomerization of 1233zd are metal oxides, halogenated metal oxides, Lewis acid metal halides, zero-valent metals, as well as combinations of these catalysts.

Where the catalyst includes a metal oxide or a halogenated metal catalyst, it may comprise a transition metal having an atomic number from about 21 to about 57, metals from Group IIIA having an atomic number of from about 13 to about 81, metals from Group VA having an atomic number of from about 51 to about 83, rare earth metals such as cerium, alkali metals from Group IA having an atomic number of from about 3 to about 36, alkali earth metals from Group IIA having an atomic number of from about 12 to about 56, or any suitable mixture or alloy of these metals.

Where the catalyst includes a Lewis acid metal halide, it may comprise transition metals having an atomic number from about 21 to about 57, metals from Group IIIA having an atomic number of from about 13 to about 81, metals from Group VA having an atomic number of from about 51 to about 83, rare earth metals such as cerium, alkali metals from Group IA having an atomic number of from about 3 to about 37, alkali earth metals from Group IIA having an atomic number of from about 12 to about 56, or any suitable mixture or alloy of these metals.

Specific examples of suitable catalysts are $AlF_3$, $Cr_2O_3$, fluorinated $Cr_2O_3$, zirconium oxide and halogenated versions thereof, or an aluminum oxide and halogenated versions thereof. In addition, the catalysts may be activated prior to use. Examples of activation procedures for several suitable catalysts may be found in U.S. Publication No. 2008-0103342, entitled "Processes for Geometric Isomerization of Halogenated Olefins," which is hereby incorporated by reference in its entirety.

The feed stream may be fed into the reactor vessel in the vapor phase. Alternately, the feed stream is fed into the reactor vessel in the liquid phase and the temperature of the heated surface within the reactor vessel causes the feed stream to vaporize. Examples of suitable temperatures for the heated surface within the reactor vessel are greater than about 50° C., greater than about 100° C., greater than about 250° C., between about 50° C. and about 400° C., between about 50° C. and about 350° C., between about 100° C. and about 350° C., between about 150° C. and about 350° C., between about 200° C. and about 300° C., about 50° C., about 100° C., about 150° C., about 200° C., about 250° C., or about 300° C.

The pressure in the reactor vessel during the isomerization reaction may be at or slightly above atmospheric pressure, or it may be between atmospheric pressure and 300 psi, between atmospheric pressure and 200 psi, or between atmospheric pressure and 100 psi. In continuous-type reactor vessels, the feed stream may be fed in at slightly above atmospheric pressure or within any of the elevated pressure ranges specified above, or the feed stream may be fed into the reactor vessel below atmospheric pressure and the exit of the reactor vessel may be placed under vacuum.

In some embodiments of the invention, a method of converting 1233zd(E) to 1233zd(Z) comprises the steps of providing a feed stream comprising or consisting essentially of 1233zd(E) or a mixture of E and Z isomers having less than about 5 wt % 1233zd(Z). In other embodiments, the feed stream has less than about 7 wt % 1233zd(Z) or less than about 9 wt % 1233zd(Z). The feed stream is contacted with a heated surface for a sufficient amount of time such that the desired amount of 1233zd(Z) is present in the product stream. In some embodiments, the product stream consists essentially of 1233zd(Z) and 1233zd(E). The amount of 1233zd(Z) in the product stream may be greater than about 5 wt %, greater than about 7 wt %, greater than about 9 wt %, greater than about 10 wt %, greater than about 12 wt %, greater than about 15 wt %, between about 5 wt % and about 20 wt %, between about 5 wt % and about 17 wt %, between about 5 wt % and about 15 wt %, between about 5 wt % and about 12 wt %, or about 5 wt %, about 7 wt %, about 9 wt %, about 10 wt %, about 12 wt %, or about 15 wt %. In some embodiments, the amount of 1233zd (Z) in the product stream corresponds to the equilibrium ratio of 1233zd(Z), whereas in other embodiments the amount of 1233zd(Z) corresponds to less than the equilibrium ratio of 1233zd(Z).

In other embodiments of the invention, a method of converting 1233zd(Z) to 1233zd(E) comprises the steps of providing a feed stream comprising or consisting essentially of 1233zd(Z) or a mixture of (E) and (Z) isomers having more than about 15 wt % 1233zd(Z). In other embodiments, the feed stream has more than about 25 wt % 1233zd(Z), more than about 50 wt % 1233zd(Z), more than about 75 wt % 1233zd(Z), more than about 85 wt % 1233zd(Z), more than about 90 wt % 1233zd(Z), or more than about 95 wt % 1233zd(Z). The feed stream is contacted with a heated surface for a sufficient amount of time such that the desired amount of 1233zd(E) is present in the product stream. In some embodiments, the product stream consists essentially of 1233zd(Z) and 1233zd(E). The amount of 1233zd(E) in the product stream may be greater than about 15 wt %, greater than about 25 wt %, greater than about 40 wt %, greater than about 50 wt %, greater than about 55 wt %, greater than about 60 wt %, greater than about 70 wt %, greater than about 80 wt %, greater than about 90 wt %, or greater than about 95 wt %. In some embodiments, the wt % of 1233zd(E) in the product stream is about 55 wt %, about 60 wt %, about 65 wt %, or about 70 wt %. In some embodiments, the wt % of 1233zd(E) in the product stream is at least about 1 wt %, at least about 3 wt %, at least about 5 wt %, at least about 7 wt %, at least about 9 wt %, at least about 10 wt %, at least about 15 wt %, at least about 20 wt %, at least about 30 wt %, at least about 40 wt %, at least about 50 wt %, at least about 75 wt %, at least about 80 wt %, at least about 85 wt %, at least about 90 wt %, or at least about 95 wt % higher than the wt % of 1233zd(E) present in the feed stream. In some embodiments, the amount of 1233zd (Z) in the product stream is between about 5 wt % and about 50 wt %, between about 10 wt % and about 40 wt %, or between about 20 wt % and about 40 wt %. In some embodiments, the amount of 1233zd(E) in the product stream corresponds to the equilibrium ratio of 1233zd(E), whereas in other embodiments the amount of 1233zd(E) corresponds to less than the equilibrium ratio of 1233zd(E).

In some embodiments of the invention, a method of converting between (E)1-chloro-3,3,3-trifluoropropene and (Z)1-chloro-3,3,3-trifluoropropene, comprises providing a vaporized feed stream comprising or consisting essentially of one or both isomers of 1-chloro-3,3,3-trifluoropropene. The feed stream has a first ratio of (E) isomer to (Z) isomer. As discussed herein, a temperature controlled reaction vessel may be used that includes an interior surface, a first opening, a second opening, a pathway fluidly connecting the first and second openings, and a packing material disposed in the pathway. The heated surface may include the interior surface and the packing material contacting the feed stream with the heated surface that is maintained at a desired temperature. The desired temperature may be any of the temperature ranges mentioned herein, for example between 50° C. and 350° C. The feed stream may be contacted with the heated surface for a period of time sufficient to convert the feed stream into a product stream having a second ratio of (E) to (Z) isomer.

Because the methods described above include equilibrium reactions, the product streams will comprise a mixture of both isomers of 1233zd. However, because of differing physical properties (e.g., different boiling points), the two isomers may be separated from one another using a separation process. For example, the product stream from any of the above methods may be fed directly into a suitable distillation operation. In other embodiments, the product stream is fed through an intermediate unit operation prior to being fed into the distillation column or is stored prior to being fed through the distillation column. In some embodiments, the distillation process yields substantially pure, or pure, separated product streams of 1233zd(Z) and 1233zd(E). Where only one of the (Z) or (E) separated product streams are commercially desirable, all or a portion of the undesirable separated product stream may be recycled back into an isomerization process.

In some embodiments in which the product streams of the above methods comprises additional compounds other than the isomers of 1233zd, the additional compounds may have similar properties (e.g., boiling points) to one of the (Z) or (E) isomers that may cause the additional compounds to be captured in either or both of the (Z) or (E) product streams. In such embodiments, the (Z) or (E) product stream(s) with the additional compounds may be useful for particular applications. In other embodiments, the product stream(s) with the additional compounds may be discarded, a portion of the product stream(s) with the additional compounds may be recycled into the feed stream for one of the isomerization methods, and/or a portion of the product stream(s) may be sent to an additional unit operation that will separate the 1233zd from one or all of the additional compounds. In other embodiments, the additional compounds may have properties that differ from both the 1233zd(Z) and the 1233zd(E), allowing the 1233zd(Z), the 1233zd(E) and the additional compounds to be separated into three or more product streams.

Further, in some methods of producing 1233zd, the product stream includes both the (Z) and (E) isomers along with byproducts and unreacted materials. In some such embodiments, a separation operation (e.g., a distillation operation) is used to separate the (Z) and (E) product streams from one another, but many of the byproducts and unreacted materials have boiling points and/or other properties that cause at least a portion of the byproducts and unreacted materials to be captured in one of the product streams, for example in the 1233zd(E) product stream. In such embodiments, the 1233zd (E) product stream may be captured for other uses, and the pure or substantially pure 1233zd(Z) product stream may be used as the feed stream for one of the isomerization methods described above in order to produce a product stream consisting essentially of a mixture of (E) and 1233zd(Z). As described above, the product stream from the isomerization method may then be fed into a separation process in order to yield separate product streams for the (Z) and (E) isomers.

In some embodiments, a 1233zd production operation is connected directly or indirectly with a first separation operation to separate the (Z) isomer, the (E) isomer and the byproducts and unreacted materials. The first separation operation may be directly or indirectly connected with an isomerization operation, which in turn may be directly or indirectly connected with a second separation operation. As used herein, "indirectly connected" includes both being connected via another unit operation as well as embodiments in which the product stream is stored for a time prior to being fed to the next operation.

Example 1

A sample of 99.9% pure 1233zd(E) was fed through a MONEL™ tube that was packed with $AlF_3$. The tube was maintained at a temperature of 200° C. by means of a furnace. The 1233zd(E) was passed through the tube at near ambient pressure and was captured as it exited the tube in a cylinder that was cooled in dry ice. Then the same starting material was again passed through the tube with the furnace set to 300° C. After each temperature trial a sample of the captured material was taken and analyzed by GC. The sample passed over the AlF$_3$ at 200° C. had converted to 4.4% 1233zd(Z) and was still clear. The sample that was passed over the catalyst at 300° C. was slightly yellow in color and had converted to 10.8% 1233zd(Z).

Example 2

A sample of 99.9% pure 1233zd(E) was passed through a MONEL™ tube that was packed with 206 gm of stainless steel packing. The tube was heated to 300° C. in a furnace and the 1233zd(E) was passed through the tube and collected at the tube exit in a cylinder chilled in dry ice. The collected material was recycled through the reaction tube to investigate if thermal equilibrium had been achieved. The recycling of the collected material was done for a total of 4 passes through the reaction tube. Samples were taken after each pass and the analysis of those samples is given in Table 1. All of the samples collected in this experiment were clear in color. This example shows that it is possible to convert 1233zd(E) thermally to 1233zd(Z) with a very high yield.

TABLE 1

| | Area Percent by GC | | |
|---|---|---|---|
| | 1233zd(E) | 1233zd(Z) | Other |
| Initial | 99.9 | — | 0.1 |
| 1$^{st}$ Pass | 97.8 | 2.1 | 0.1 |
| 2$^{nd}$ Pass | 95.7 | 4.2 | 0.1 |
| 3$^{rd}$ Pass | 94.4 | 5.5 | 0.1 |
| 4$^{th}$ Pass | 93.3 | 6.6 | 0.2 |

Example 3

Conversion of 1233zd(E) into 1233zd(Z) was performed using a MONEL™ reactor (ID 2 inch, length 32 inch) equipped with a MONEL™ preheater (ID 1 inch, length 32 inch) which was filled with Nickel mesh to enhance heat transfer. The reactor was filled with 1.5 L of pelletized fluorinated Cr$_2$O$_3$ catalyst. Nickel mesh was placed at the top and at the bottom of reactor to support the catalyst. A multi-point thermocouple was inserted at the center of the reactor. 99.9% pure 1233zd(E) was introduced into the reactor at the rate of 0.8 lb/hr. The feed was vaporized prior entering the reactor preheater. The reactor temperature for this experiment was set to 250° C. The temperature gradient throughout the reactor never exceeded 3-5° C. Samples of reaction products were taken every hour and GC analysis of those samples is given in Table 2.

TABLE 2

| Reaction time | Area Percent by GC | | |
|---|---|---|---|
| (hr) | 1233zd(E) | 1233zd(Z) | Other |
| 1 | 90.34 | 8.56 | 1.10 |
| 2 | 90.47 | 8.62 | 0.91 |
| 3 | 90.63 | 8.50 | 0.87 |
| 4 | 90.16 | 8.96 | 0.88 |
| 5 | 90.17 | 8.95 | 0.87 |
| 6 | 90.11 | 9.01 | 0.89 |

TABLE 2-continued

| Reaction time | Area Percent by GC | | |
|---|---|---|---|
| (hr) | 1233zd(E) | 1233zd(Z) | Other |
| 7 | 90.13 | 8.98 | 0.89 |
| 8 | 90.11 | 9.00 | 0.89 |
| 9 | 90.13 | 8.98 | 0.89 |
| 10 | 90.41 | 8.69 | 0.90 |

Example 4

Example 3 was repeated except the reaction temperature was set to 300° C. The temperature gradient throughout the reactor never exceeded 3-5° C. Samples of reaction products were taken every hour and GC analysis of those samples is given in Table 3.

TABLE 3

| Reaction time | Area Percent by GC | | |
|---|---|---|---|
| (hr) | 1233zd(E) | 1233zd(Z) | Other |
| 1 | 88.95 | 9.35 | 1.70 |
| 2 | 87.78 | 9.76 | 2.45 |
| 3 | 87.59 | 9.90 | 2.52 |
| 4 | 87.53 | 10.00 | 2.46 |
| 5 | 87.46 | 9.97 | 2.57 |
| 6 | 87.50 | 10.06 | 2.44 |
| 7 | 87.51 | 9.97 | 2.52 |
| 8 | 87.37 | 10.22 | 2.41 |
| 9 | 87.62 | 10.02 | 2.36 |
| 10 | 87.45 | 10.12 | 2.43 |

Example 5

Conversion of 1233zd(Z) into 1233zd(E) was performed using a MONEL™ reactor (ID 2 inch, length 32 inch) equipped with a MONEL™ preheater (ID 1 inch, length 32 inch) which was filled with Nickel mesh to enhance heat transfer. The reactor was filled with 1.5 L of pelletized fluorinated Cr$_2$O$_3$ catalyst. Nickel mesh was placed at the top and at the bottom of reactor to support the catalyst. A multi-point thermocouple was inserted at the center of the reactor. A feed containing about 10.0 wt % 1233zd(E) and 86.3 wt % 1233zd(Z) was introduced into the reactor at the rate of 0.7 lb/hr. The feed was vaporized prior to entering the reactor preheater. The reactor temperature for this experiment was varied between 100° C. and 200° C. The temperature gradient throughout the reactor never exceeded 3-5° C. Samples of reaction products were taken every hour and GC analysis of those samples is given in Table 4.

TABLE 4

| Reaction Temperature | Area Percent by GC | | |
|---|---|---|---|
| ° C. | 1233zd(E) | 1233zd(Z) | Others |
| Initial | 10.0 | 86.3 | 3.7 |
| 103 | 69.6 | 27.9 | 2.5 |
| 104 | 69.8 | 27.9 | 2.4 |
| 128 | 70.2 | 27.6 | 2.2 |
| 128 | 65.0 | 32.8 | 2.2 |
| 128 | 62.8 | 35.0 | 2.2 |
| 128 | 60.9 | 36.9 | 2.2 |

TABLE 4-continued

| Reaction Temperature | Area Percent by GC | | |
|---|---|---|---|
| °C. | 1233zd(E) | 1233zd(Z) | Others |
| 151 | 60.8 | 37.1 | 2.1 |
| 151 | 61.8 | 36.2 | 2.0 |
| 151 | 62.4 | 35.6 | 2.0 |
| 151 | 58.9 | 39.0 | 2.1 |
| 181 | 62.2 | 35.8 | 2.0 |
| 199 | 68.3 | 29.4 | 2.3 |

Comparative Example

A 110-mL glass pressure vessel was purged with nitrogen to remove air and charged with 13.75 g of 99.7% pure 1233zd (E) and 0.07 g of bromine (0.4 mol % relative to 1233zd(E)). The mixture was irradiated at room temperature with a 60-W broad spectrum light for 17.75 hours. Analysis indicated 95.85% 1233zd(E) and 3.57% of the 1233zd(Z). The experiment was repeated except that 2 mol % of bromine relative to 1233zd(E) was used. After irradiation for 22 hours, analysis showed 95.1% of the (E)isomer and 3.27% of the (Z)isomer. Thus, experimentally the thermodynamic ratio is about 95.5% (E)isomer and 3.4% (Z)isomer. To confirm this, 14.86 g of a mixture comprised of 89.5% 1233zd(E) and 10.2% 1233zd(Z) was combined with 0.4 g of bromine and the mixture irradiated as above for 19 hours. Analysis indicated 95.5% 1233zd(E) and 3.2% 1233zd(Z). The use of the reagent bromine in this Comparative Example is in contrast to Examples 1-5, which are isomerization reactions that do not require reagents.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. In the foregoing, all temperatures are set forth uncorrected in degrees Celsius and, all parts and percentages are by weight, unless otherwise indicated.

From the foregoing description, one skilled in the art can ascertain the essential characteristics of this invention and, without departing from the spirit and scope thereof, can make various changes and modifications of the invention to adapt it to various usages and conditions.

The invention claimed is:

1. A method of converting (E)1-chloro-3,3,3-trifluoropropene into (Z)1-chloro-3,3,3-trifluoropropene, comprising:
    providing a feed stream consisting essentially of (E)1-chloro-3,3,3-trifluoropropene or a mixture of (E)1-chloro-3,3,3-trifluoropropene and (Z)1-chloro-3,3,3-trifluoropropene having less than about 5 wt % (Z)1-chloro-3,3,3-trifluoropropene;
    contacting the feed stream with a heated surface that is maintained between 150° C. and 350° C. for a period of time sufficient to convert at least a portion of the (E)1-chloro-3,3,3-trifluoropropene to (Z)1-chloro-3,3,3-trifluoropropene to produce a product stream; and
    distilling the product stream to separate the (E) and (Z) isomers from one another.

2. The method of claim 1, further comprising the step of providing a temperature controlled reaction vessel that includes an interior surface, a first opening, a second opening, a pathway fluidly connecting the first and second openings, and a packing material disposed in the pathway, wherein the heated surface includes the interior surface and the packing material.

3. The method of claim 1, wherein the feed stream has been vaporized before the step of contacting the feed stream with the heated surface.

4. The method of claim 1, wherein the feed stream is vaporized after the step of contacting the feed stream with the heated surface.

5. The method of claim 1, wherein sufficient (E)1-chloro-3,3,3-trifluoropropene is converted to (Z)1-chloro-3,3,3-trifluoropropene to yield a product stream having more than 5 wt % (Z)1-chloro-3,3,3-trifluoropropene.

6. The method of claim 1, wherein the product stream has between about 5 wt % and about 17 wt % (Z)1-chloro-3,3,3-trifluoropropene.

7. The method of claim 1, wherein the heated surface includes the outer surface of a packing material.

8. The method of claim 7, wherein the packing material is a catalyst material.

9. The method of claim 8, wherein the catalyst material is a metal oxide, halogenated metal oxide, a Lewis acid metal halide, or a zero-valent metal, or a mixture or alloy thereof.

10. The method of claim 8, wherein the catalyst material is $AlF_3$, fluorinated $Cr_2O_3$, or $Cr_2O_3$.

11. The method of claim 1, wherein the product stream consists essentially of (E)1-chloro-3,3,3-trifluoropropene and (Z)1-chloro-3,3,3-trifluoropropene.

12. The method of claim 1, wherein the method of converting is reagent-free.

13. A method of converting (Z)1-chloro-3,3,3-trifluoropropene into (E)1-chloro-3,3,3-trifluoropropene, comprising:
    providing a feed stream consisting essentially of (Z)1-chloro-3,3,3-trifluoropropene or a mixture of (E)1-chloro-3,3,3-trifluoropropene and (Z)1-chloro-3,3,3-trifluoropropene having more than about 15 wt % (Z)1-chloro-3,3,3-trifluoropropene;
    contacting the feed stream with a heated surface that is maintained between 50° C. and 350° C. for a period of time sufficient to convert at least a portion of the (Z)1-chloro-3,3,3-trifluoropropene to (E)1-chloro-3,3,3-trifluoropropene to produce a product stream; and
    distilling the product stream to separate the (E)1-chloro-3,3,3-trifluoropropene and (Z)1-chloro-3,3,3-trifluoropropene from one another.

14. The method of claim 13, wherein the amount of (E)1-chloro-3,3,3-trifluoropropene in the product stream is at least 5 percentage points higher than the wt % of (E)1-chloro-3,3,3-trifluoropropene in the feed stream.

15. The method of claim 13, wherein the product stream has between about 5 wt % and about 50 wt % (Z)1-chloro-3,3,3-trifluoropropene.

16. The method of claim 13, wherein the product stream has between about 50 wt % and about 95 wt % (E)1-chloro-3,3,3-trifluoropropene.

17. The method of claim 13, further comprising the step of providing a temperature controlled reaction vessel that includes an interior surface, a first opening, a second opening, a pathway fluidly connecting the first and second openings, and a packing material disposed in the pathway, wherein the heated surface includes the interior surface and the packing material.

18. The method of claim 13, wherein the feed stream has been vaporized before the step of feeding the feed stream into the reactor vessel.

19. The method of claim 13, wherein the feed stream is vaporized after the step of feeding the feed stream into the reactor vessel.

20. The method of claim 13, wherein the reactor vessel is packed with a packing material.

21. The method of claim 20, wherein the packing material is a catalyst material.

22. The method of claim 21, wherein the catalyst material is a metal oxide, a halogenated metal oxide, a Lewis acid metal halide, or a zero-valent metal, or a mixture or alloy thereof.

23. The method of claim 21, wherein the catalyst material is $AlF_3$, fluorinated $Cr_2O_3$, or $Cr_2O_3$.

24. The method of claim 13, wherein the product stream consists essentially of (E)1-chloro-3,3,3-trifluoropropene and (Z)1-chloro-3,3,3-trifluoropropene.

25. The method of claim 13, wherein the method of converting is reagent-free.

* * * * *